US006838670B2

(12) United States Patent
Lewis et al.

(10) Patent No.: US 6,838,670 B2
(45) Date of Patent: Jan. 4, 2005

(54) METHODS AND SYSTEM FOR ULTRASONIC THERMOGRAPHIC NON-DESTRUCTIVE EXAMINATION FOR ENHANCED DEFECT DETERMINATION

(75) Inventors: Oscar O. Lewis, Humble, TX (US); Thomas C. Schreiner, Muelheim (DE); Miguel A. Felix, Irwin, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 64 days.

(21) Appl. No.: 10/292,293

(22) Filed: Nov. 12, 2002

(65) Prior Publication Data

US 2004/0089811 A1 May 13, 2004

(51) Int. Cl.[7] .............................................. G01N 25/72
(52) U.S. Cl. .................................. 250/341.6; 250/341.1
(58) Field of Search ......................... 250/341.6, 341.1, 250/341.8, 330, 332, 334, 341, 347, 358.1, 359.1, 338.1, 338.3; 356/237, 381; 348/571; 374/5, 7, 124

(56) References Cited

U.S. PATENT DOCUMENTS

| 5,111,048 | A | * | 5/1992 | Devitt et al. ................. 250/342 |
| 6,097,482 | A | * | 8/2000 | Smith et al. ............. 356/237.1 |
| 6,104,116 | A | | 8/2000 | Fuller et al. |
| 6,236,049 | B1 | | 5/2001 | Thomas et al. |
| 6,346,704 | B2 | * | 2/2002 | Kenway .................... 250/341.6 |
| 6,399,948 | B1 | * | 6/2002 | Thomas et al. .......... 250/341.6 |
| 6,541,778 | B1 | * | 4/2003 | Jankowiak et al. ...... 250/461.1 |
| 6,593,574 | B2 | * | 7/2003 | Thomas et al. .......... 250/341.6 |
| 6,690,016 | B1 | * | 2/2004 | Watkins et al. .......... 250/341.7 |
| 6,698,288 | B2 | * | 3/2004 | Shirzad et al. ................. 73/577 |
| 2002/0018510 | A1 | * | 2/2002 | Murphy et al. ............... 374/45 |
| 2002/0044679 | A1 | * | 4/2002 | Shepard ...................... 382/141 |
| 2003/0229458 | A1 | * | 12/2003 | Alfano et al. ................. 702/40 |

OTHER PUBLICATIONS

Shepard (Thermal Wave Imaging, Inc.)—Article titled "Introduction to Pulsed Thermography for NDT".
Ahmed, et al (Thermal Wave Imaging, Inc.); Article titled "Active Thermographic Inspection of Combustion Turbine Engine Components".
Advertisement by Thermal Wave Imaging, Inc. for Echo Therm—Setting the Standard for Thermographic NDE!.
Advertisement by Thermal Wave Imaging, Inc. for MOSIAQ—Are you Puzzled by Thermographic NDT?.
Advertisement by Thermal Wave Imaging, Inc. for Thermo-Scope—Thermography is In Your Hands!.
Advertisement by Thermal Wave Imaging, Inc. for Transition Panels.
Advertisement by Thermal Wave Imaging, Inc. for Ni Alloy Blades and Vanes.
Advertisement by Thermal Wave Imaging, Inc. for TBC Coatings.

* cited by examiner

*Primary Examiner*—Constantine Hannaher
*Assistant Examiner*—Otilia Gabor

(57) ABSTRACT

A method and system (100) for enhancing the determination of the presence of a surface breaking or subsurface defect with an object (114) under test are provided (FIG. 1). The method can include transferring ultrasonic energy to an object (114) under test and sensing images (514, 514') of the object (114) under test before and after transferring ultrasonic energy to the object (114) with an infrared thermography camera (112). An increase in temperature gradients in the areas adjacent a defect (516, 516') is shown in the images (514, 514') produced by the camera (112), which indicates the presence of the defect (516, 516'). The temperature gradients in the area of the defect (516, 516') and images of the defect (516, 516') can be displayed to enable users to determine the temperature gradient and thus the extent of the defect (516, 516'). Digital images (514, 514') of the before and after transferring ultrasonic energy can be superimposed (514") to identify and illustrate the defect (516").

10 Claims, 10 Drawing Sheets

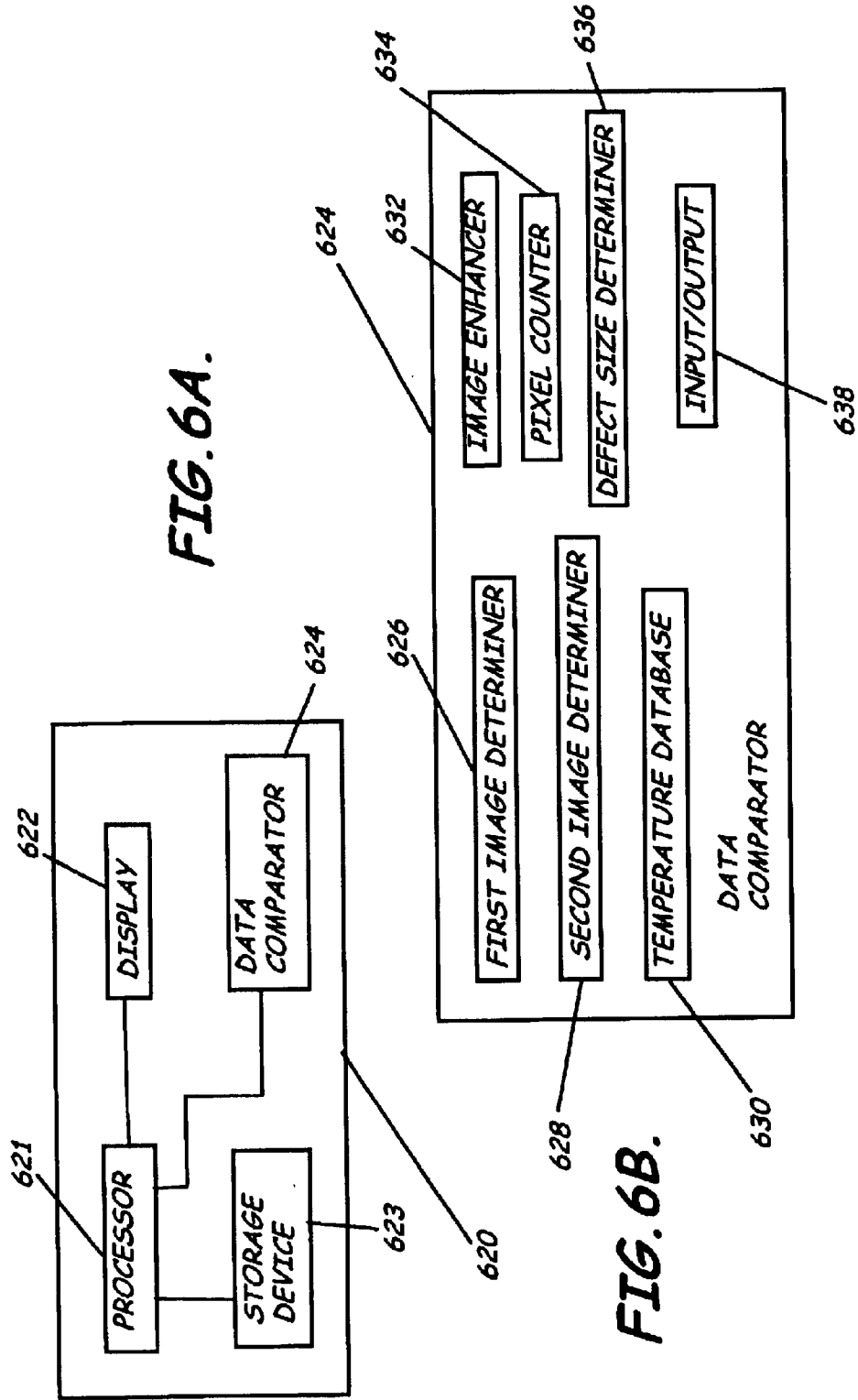

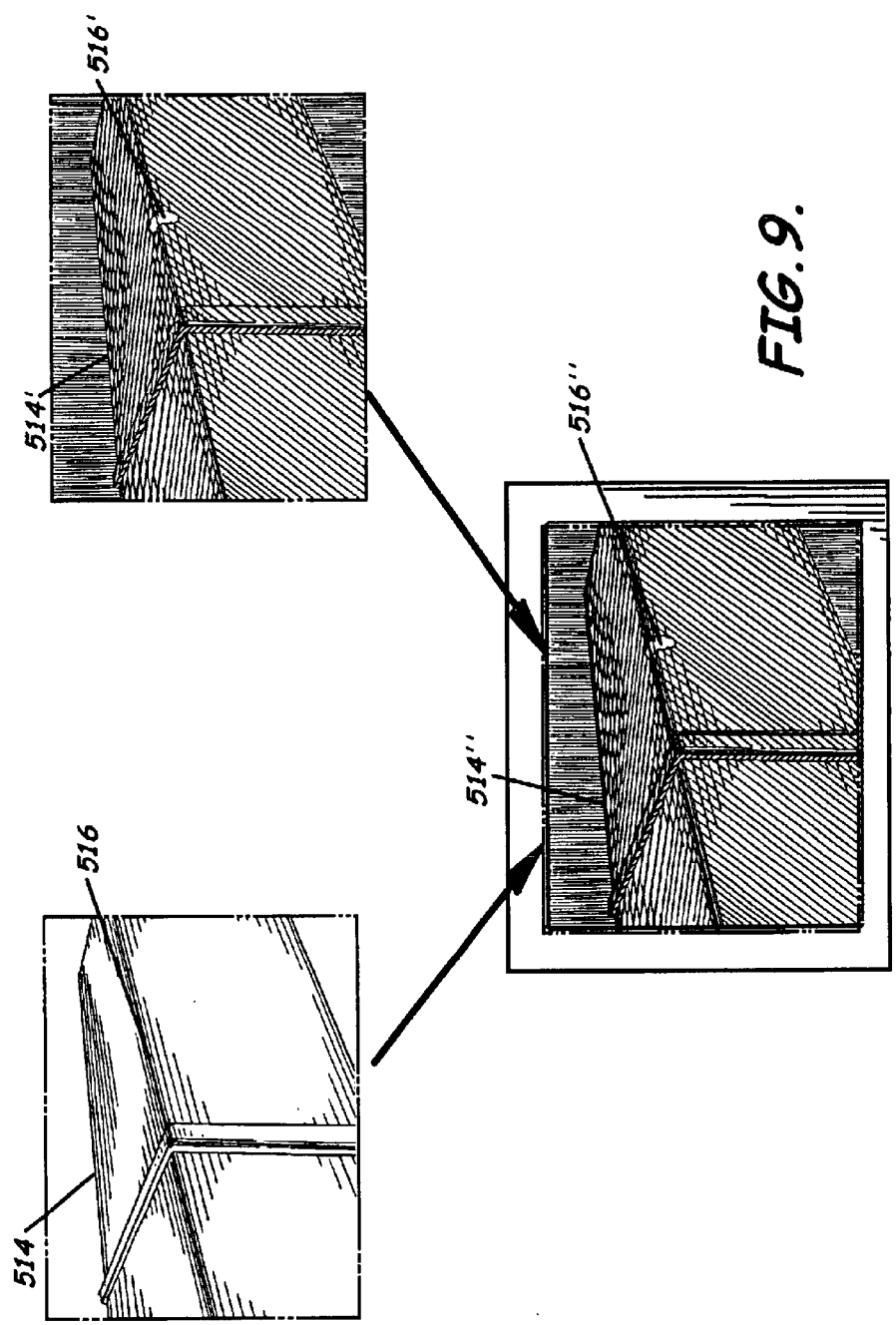

METHODS AND SYSTEM FOR ULTRASONIC THERMOGRAPHIC NON-DESTRUCTIVE EXAMINATION FOR ENHANCED DEFECT DETERMINATION

FIELD OF THE INVENTION

This invention relates to non-destructive testing methods and systems, and, more particularly, methods and systems for enhancing the determination of the presence of a defect in a material.

BACKGROUND OF THE INVENTION

In the power generation industry, various types of non-destructive tests are often used to determine if defects are present in an object. Non-destructive test methods that have been used in the past include liquid penetration, magnetic particle, eddy current, radiography, and ultrasound. These test methods tend to be time consuming and expensive to perform. In recent years, it has become more important to develop inspection techniques which optimize the efficiency of testing by reducing costs and inspection time.

One such example of a recently developed inspection method can be found in U.S. Pat. No. 6,236,049 by Thomas, et al. titled "Infrared Imaging of Ultrasonically Excited Subsurface Defects in Materials." This patent describes the use of infrared or thermal imaging of ultrasonically excited subsurface defects in a material. A source for ultrasound is used to send sound waves to a component, while images of the component are captured with a thermal imaging camera. Vibrational energy from the sound in the material causes defects in the component to heat up and become visible in the images generated by the camera.

The Thomas '049 patent also describes the use of a coupler at the end of a transducer that is used to transfer the sound waves from the source to the component. The coupler prevents the transducer from bouncing or walking along the component. Applicants have recognized that a disadvantage of using a coupler is that a portion of the vibrational energy is transferred into the component, and a rather large amount of vibrational energy is lost. The use of the coupler makes the system less efficient.

As quality assurance becomes more important, particularly in inspection, a need exists to not only determine if a defect is present in an object under test, but to also inexpensively determine the severity of the defect.

SUMMARY OF THE INVENTION

In view of the foregoing, the present invention advantageously provides methods of enhancing the determination of the presence of a surface breaking or a subsurface defect in an object under test using ultrasonic thermography. The present invention additionally advantageously provides methods and systems that allow qualitative and quantitative information about a defect to be determined and assessed. The present invention also advantageously provides methods and systems that measure dimensions of a defect, which is difficult for other inspection techniques when the defect is located below the surface of the object under test or if the defect is very small. The present invention further advantageously provides methods and systems to record or save testing data to see trends developing in the deterioration of the object and to provide an inspection history of the object under test. The present invention still further advantageously provides methods and systems that are relatively inexpensive to implement, provide stability when mounting a component, and provide enhanced contact control of the application of energy to all types of components without the need for a coupler, e.g., direct contact.

More particularly, a method of the present invention preferably includes sensing a first test image of at least portions of an object under test. Ultrasonic energy is contactingly transferred at a preselected frequency to the object under test so that the ultrasonic energy causes an increase in friction in portions of the object adjacent a defect, which causes an increase in the temperature of the portions adjacent the defect. A second test image of the at least portions of the object under test in an infrared spectrum also is sensed. The two images are compared by identifying a different brightness level between the portions of the object representative of the increased temperature and surrounding regions thereof in the sensed second test image. The increased temperature portions define a determined presence of a defect. The sensed first and second test images, for example, can be superimposed if desired or positioned in a side-by-side relationship to enhance comparative information.

The present invention further provides a method of determining the temperature of the sensed at least portions of the object under test from the first test image and of the portions of the object adjacent the defect from the sensed second test image. The temperature distributions of the sensed first and second test images preferably are compared to further indicate the presence of a defect.

Several conditions can be varied in all embodiments of the method of enhancing the determination of the presence of a defect in an object under test. The amount of ultrasonic energy transferred to the object under test can be varied by changing the contact pressure of the ultrasonic source. In addition, the preselected time period that the ultrasonic energy is transferred through the ultrasonic source can be varied. The preselected amplitude of the ultrasonic energy can also be altered. More than one of these conditions can be altered simultaneously.

The present invention advantageously provides an alternate method of enhancing the determination of the presence of a defect in an object under test. The alternate method preferably includes positioning an adhesive device on at least portions of the object under test. The adhesive device defines a reference point, which is representative of a first defect in the object under test. A test image of the at least portions of an object under test in an infrared spectrum is sensed. The test image includes at least the reference point and a second defect, e.g., naturally occurring, occurring through the manufacturing processor, or other occurring defect. The images are compared by visibly identifying a plurality of different brightness levels between the portions of the object representative of the increased temperatures and surrounding regions thereof in the sensed test image. The increased temperature portions define a determined presence of the reference point and the second defect. The comparison of the temperature distribution in the area of the reference point with the temperature of the tested area allows the determination of defects.

The present invention also advantageously includes a system for detecting defects in an object under test. The system preferably includes a frame with an ultrasonic source mounted to the frame. The ultrasonic source is preferably adapted to be positioned to abuttingly contact an object under test, i.e., directly contact, and to transmit ultrasonic energy to the object under test at a preselected frequency.

The system further preferably includes a computer that contains a processor, a data storage device in communication with the processor, a display in communication with the processor, and a data comparator. The data comparator is associated with the computer and is adapted to compare sensed test images of the object under test.

The system also preferably includes a controller in communication with the ultrasonic source and the computer to control the positioning of the ultrasonic source responsive to the computer. An infrared thermography camera is another preferable component of the system of the present invention. The infrared thermography camera is positioned in communication with the computer and adapted to sense test images of the object under test responsive to the computer.

The system can also include a source mounting arm for enhancing detection of defects in an object under test. The source mounting arm is preferably mounted to the frame and preferably is connected to the ultrasonic source. The source mounting arm is preferably in communication with the controller to move or position the ultrasonic source responsive to the controller.

The present invention can also advantageously include an additional component added to the system for the enhanced detecting of defects in an object under test. The additional component preferably includes an adhesive device. The adhesive device is preferably adapted to be adhesively mounted to and abuttingly contact the object under test. The adhesive device used in this alternate system embodiment defines a reference point representative of a defect in the object under test. The adhesive device of the alternate system preferably includes a flexible substrate and an adhesive material positioned on the flexible substrate.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 6A is a simplified block diagram of a computer and its components of a system for enhancing the determination of defects according to an embodiment of the present invention;

FIG. 6B is a simplified block diagram of a data comparator, which is a component of the computer shown in FIG. 6A, of a system for enhancing the determination of defects according to an embodiment of the present invention;

FIG. 9 is an exploded front elevational view of the images of FIGS. 5A and 5B being superimposed on a display of a computer of a system for enhancing determination of defects according to an embodiment of the present invention.

DETAILED DESCRIPTION

The present invention will now be described more fully hereinafter with reference to the accompanying drawings, in which preferred embodiments of the invention are shown. This invention may, however, be embodied in many different applications and should not be construed as limited to the illustrated embodiments set forth herein. Rather, these illustrated embodiments are provided so that this disclosure will be thorough and complete, and will fully convey the scope of the invention to those skilled in the art. Like numbers refer to like elements throughout, and prime or double prime notation, if used, generally indicates similar elements in alternative embodiments.

Figure 1:
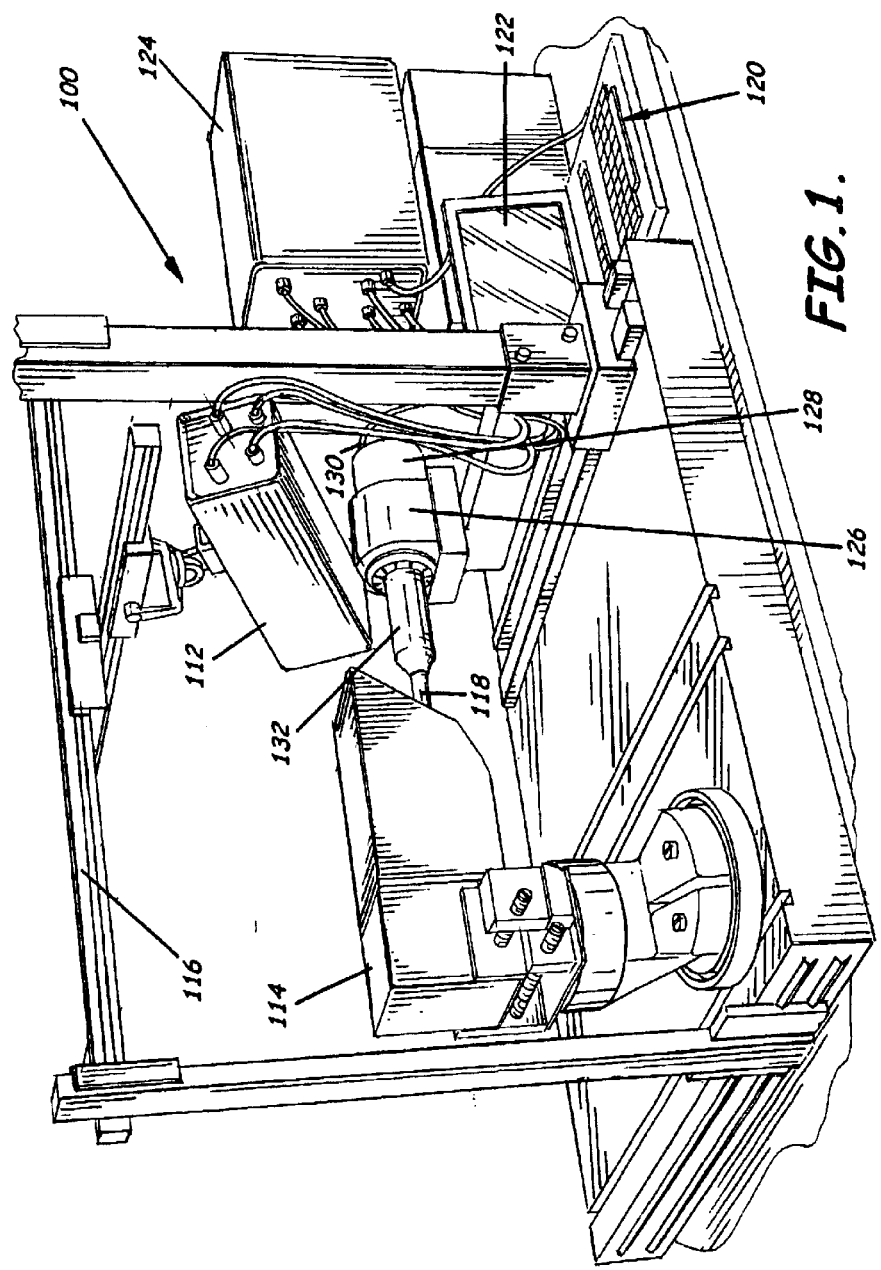
FIG. 1 is a perspective view of a system for the enhanced determination of the presence of defects in an object under test according to an embodiment of the present invention.
Figure 2:
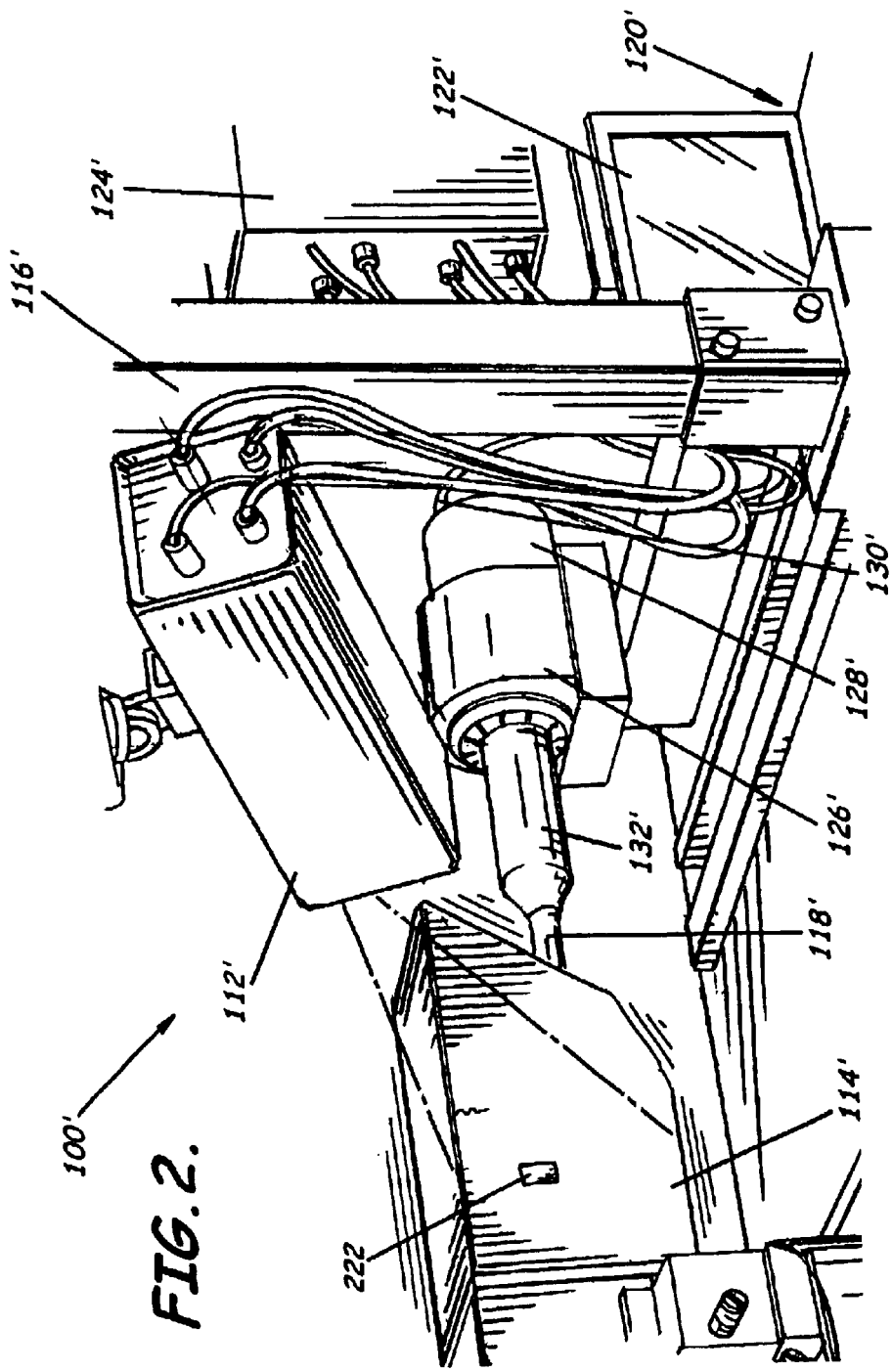
FIG. 2 is a fragmentary perspective view of a system for enhanced determination of the presence of defects in an object under test including an adhesive device adapted to be adhesively mounted to and abuttingly contact an object under test, for use as a reference point representing a defect, according to an embodiment of the present invention.
Figure 3:
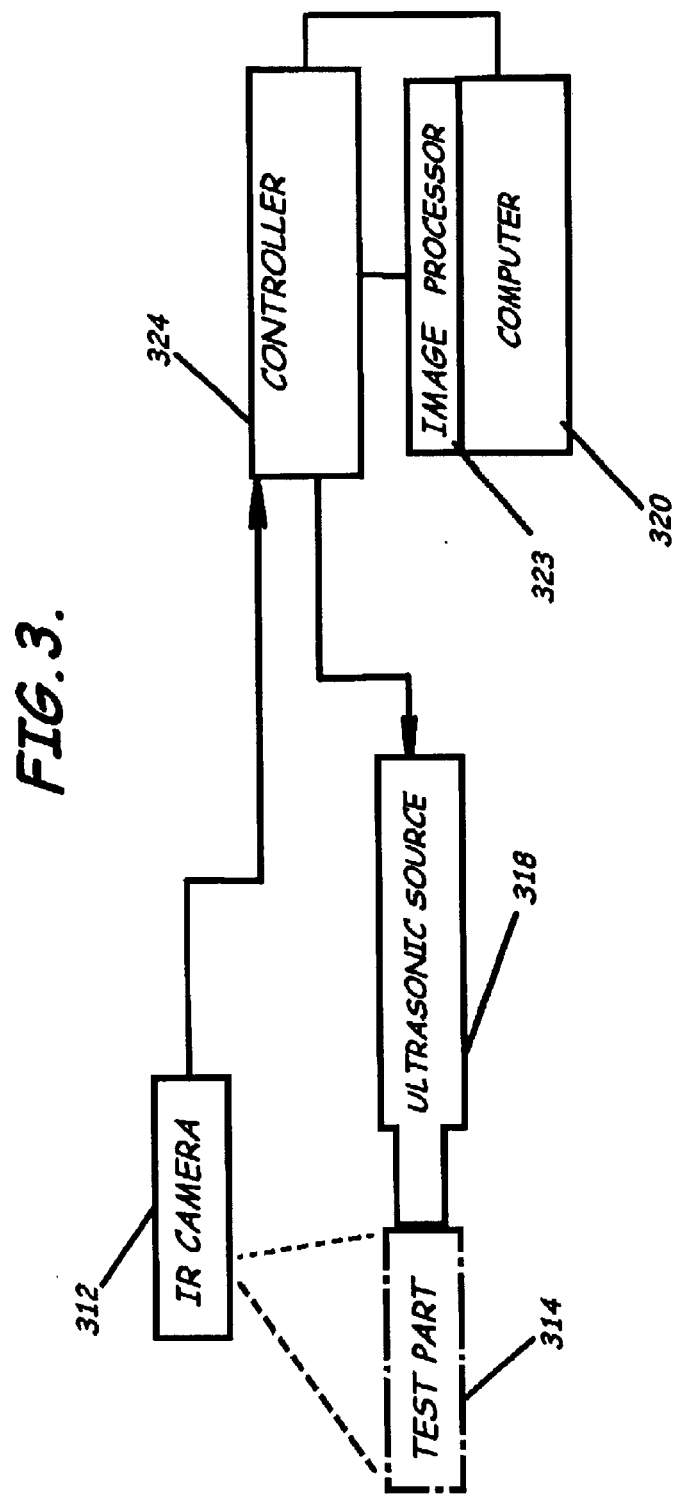
FIG. 3 is a simplified block diagram of a system for the enhanced determination of the presence of defects in an object under test according to an embodiment of the present invention.

As shown in FIGS. 1–9, the present invention advantageously provides methods of enhancing the determination of the presence of a defect in an object under test. For example, as shown in FIGS. 3 and 5A–5B, a method preferably includes sensing a first test image 514 of at least portions of an object under test 314 with an infrared thermography camera 312. Ultrasonic energy, e.g., from an ultrasonic source, is contactingly transferred at a preselected frequency to the object under test 314. The ultrasonic energy causes an increase in friction in portions of the object 314 adjacent a defect 516, which increases the temperature or vibration of the portions adjacent the defect 516. A second test image 514' of the at least portions of the object 314 under test in an infrared spectrum can also be sensed using the infrared thermography camera 312.

Figure 5A:
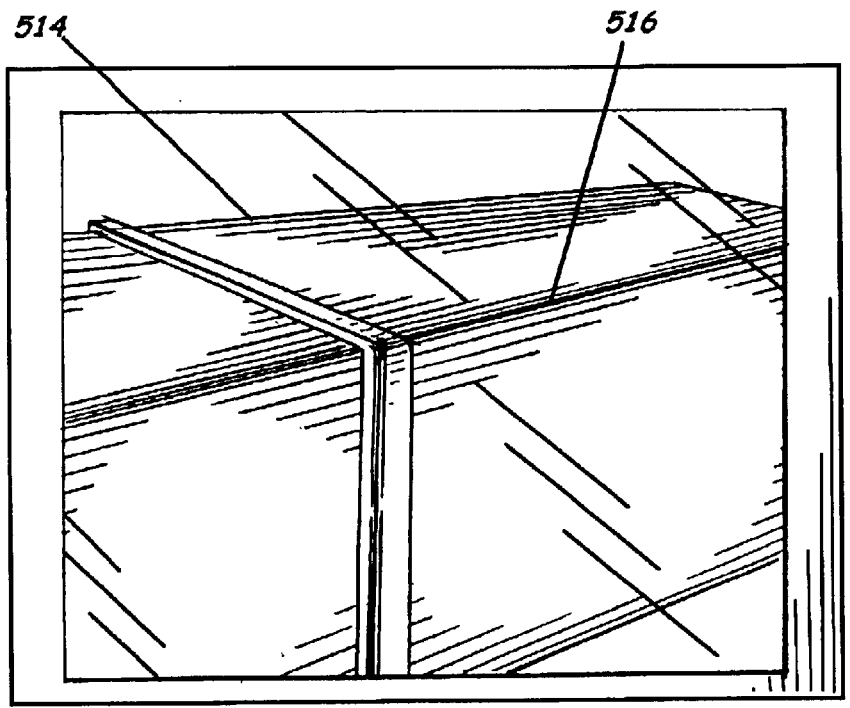
FIG. 5A is a front elevational view of an object under test shown on a display of a computer of a system for enhancing the determination of defects prior to transferring ultrasonic energy to the object under test according to an embodiment of the present invention.
Figure 5B:
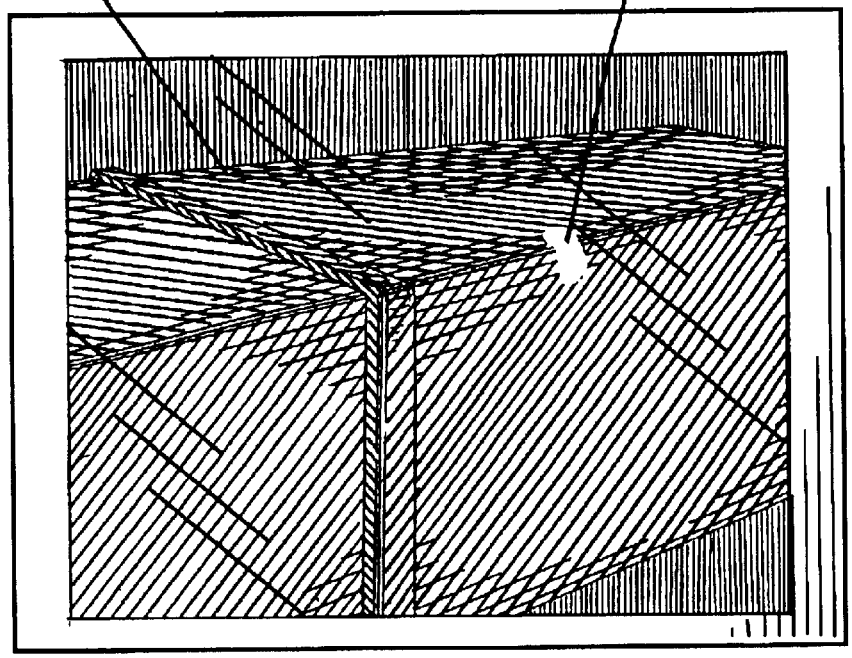
FIG. 5B is a front elevational view of a determined defect in the object under test shown on a display of a computer of a system for enhancing the determination of defects after transferring ultrasonic energy to the object under test, which is indicated by the increase level of brightness in the object under test, according to an embodiment of the present invention.
Figure 7:
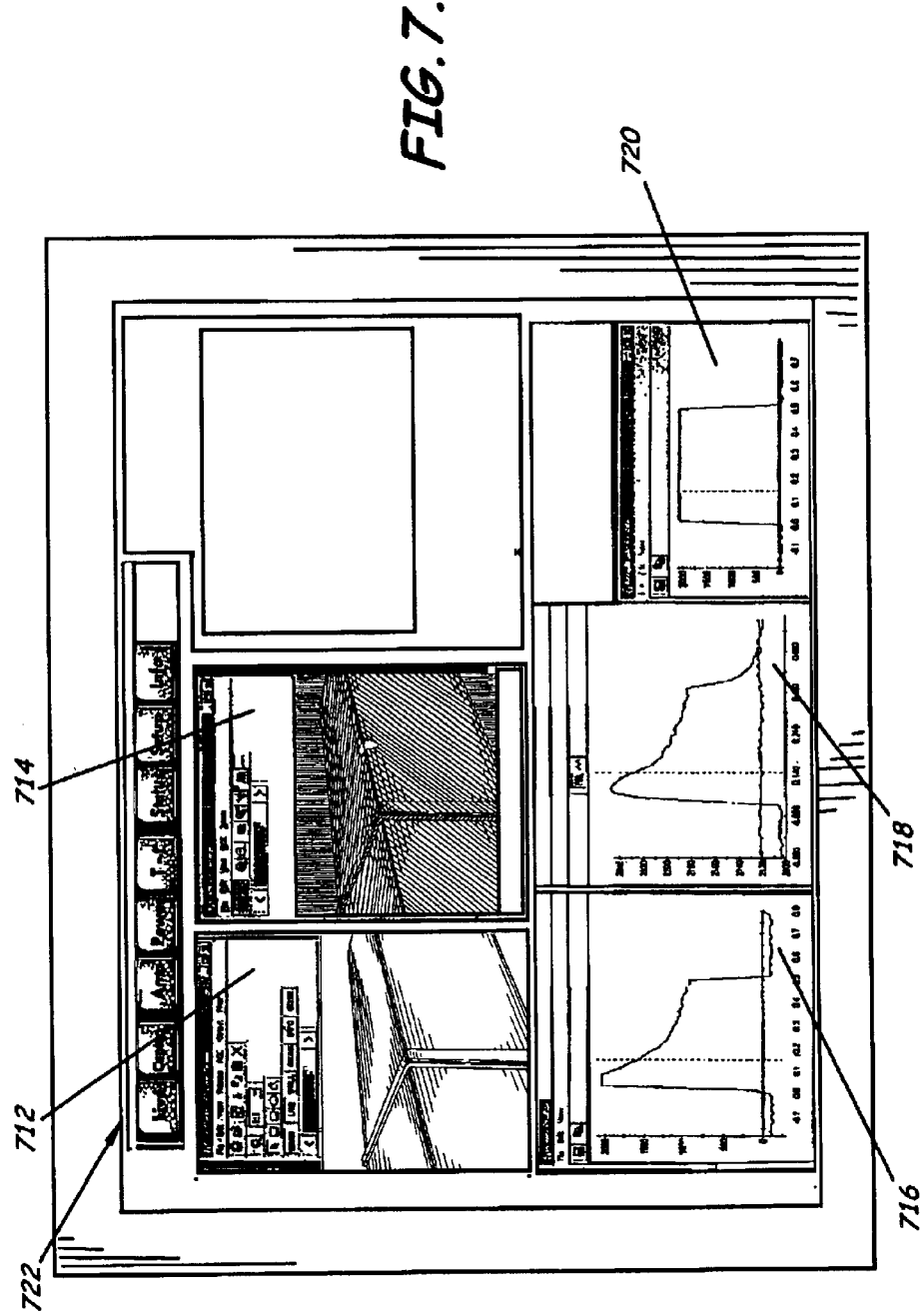
FIG. 7 is an image generated by the data comparator of a system for enhancing the determination of defects showing the various features that can be simultaneously displayed according to an embodiment of the present invention.
Figure 8:
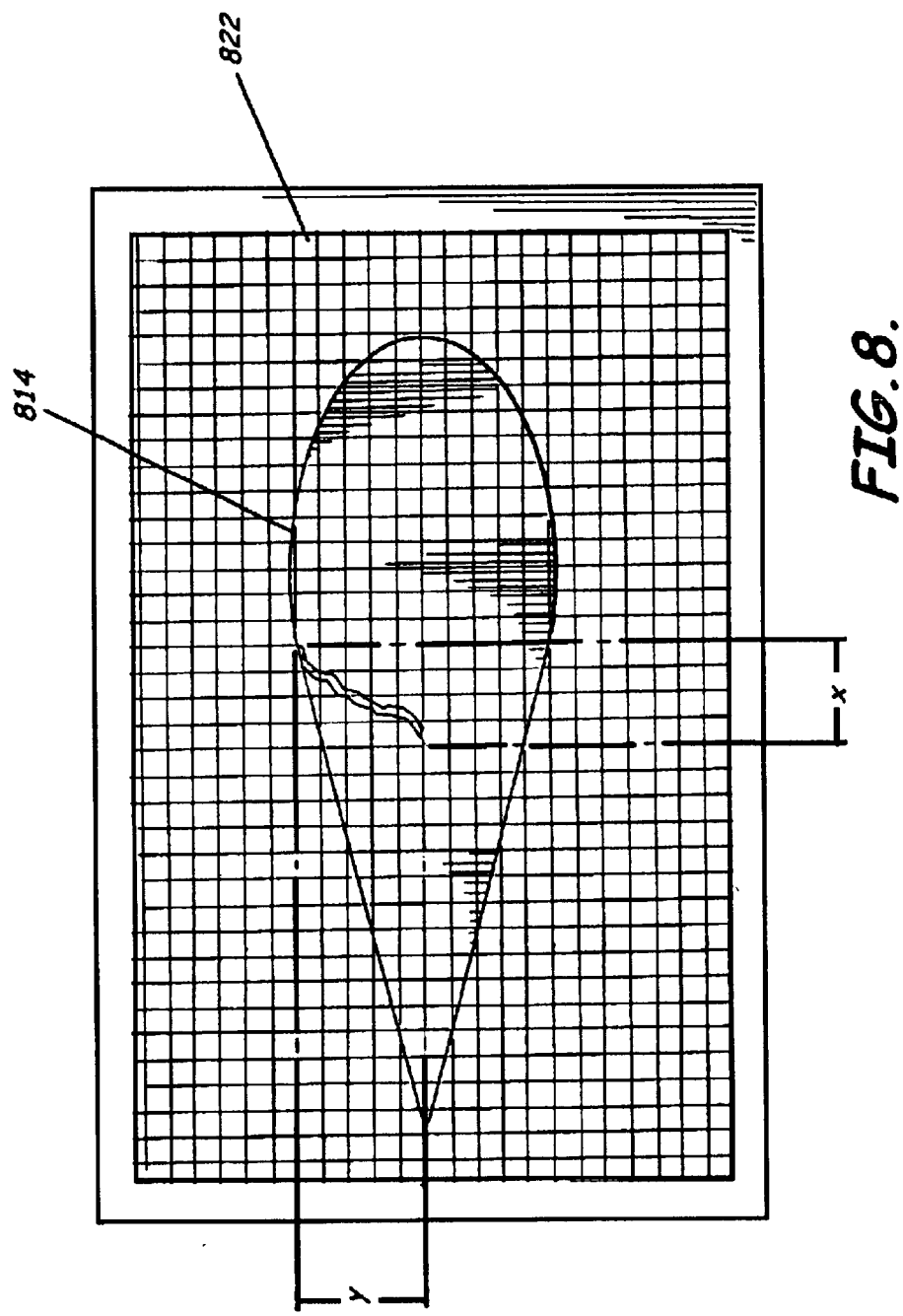
FIG. 8 is an image generated by the data comparator of a system for enhancing determination of defects, showing the number of pixel corresponding to the size of a determined defect according to an embodiment of the present invention.

As shown in FIGS. 5A and 5B, the two images 514, 514' advantageously can be compared by identifying a different brightness level between the portions of the object representative of the increased temperature in the surrounding regions thereof in the sensed second test image 514'. The increased temperature portions define a determined presence of a defect 516'. The sensed first and second test images 514, 514' can be compared in another image 514", 516", e.g., yet a third image, by superimposing the second test image 514' over the first test image 514, as shown in FIG. 9.

Figure 4A:
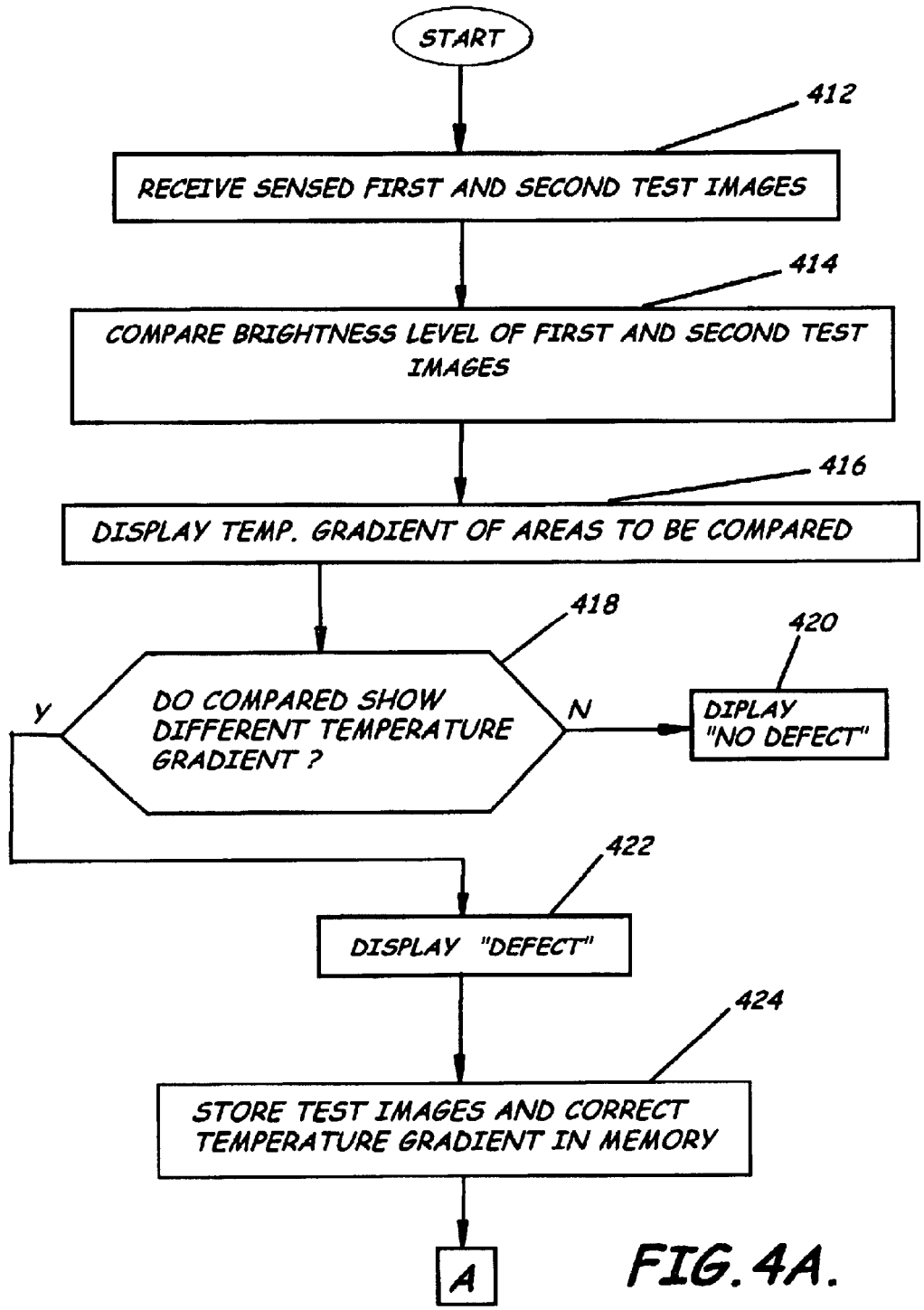
FIG. 4A is a first portion of a flow diagram of a method of enhancing the determination of defects in an object under test according to the present invention.
Figure 4B:
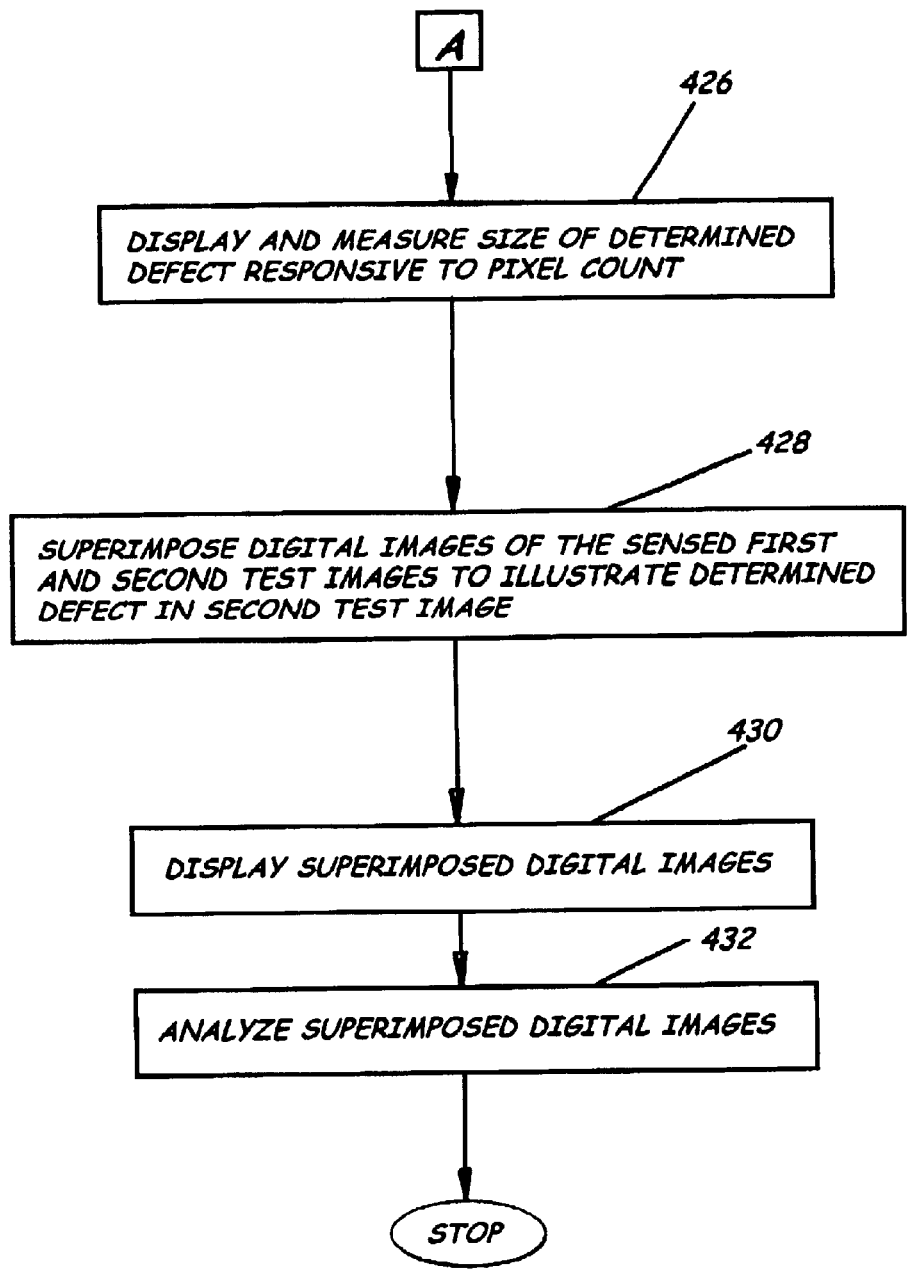
FIG. 4B is a second portion of the flow diagram shown in FIG. 4A of the method of enhancing the determination of defects in an object under test according to an embodiment of the present invention.

Comparing and superimposing the sensed images 514", 516", along with other data functions, is preferably performed by utilizing a computer software program to perform these tasks, such as shown in FIGS. 4A and 4B. Suitable software for these tasks preferably includes software developed by Indigo Systems Corp. of Santa Barbara, Calif. or Thermal Wave Imaging Inc. of Ferndale, Mich. Through the use of the software, users are able to determine the temperature of the defect 516, 516' before and after the ultrasonic energy has been transferred to the object 314 under test. The first and second test images 514, 514' are received (block 412) such as from the infrared thermography camera 312. The brightness level of the first and second test images 514, 514' are compared to determine the temperatures of the first and second test images (block 414). The temperatures of the first and second sensed images 514, 514' can be displayed (block 416). FIGS. 5A and 5B also illustrate the increase in brightness level of the second image 514 as compared to the first test images 514. The temperatures of the sensed first and second test images 514, 514' are compared to further indicate the determined presence of a defect 516, 516' (block 418). If the temperature of the second test image 514' is greater than the temperature of the first test image 514, then a defect 515, 516' is determined to be present (block 422). If the temperature of the second test image 514 is not greater than the temperature of the first test image 514, then it is determined that no defect exists (block 420). The second test image 514' can be saved to a storage device 623 in a file format (block 424). The second test image 514' can be displayed to enable measuring the size of a determined defect 516' responsive to count of pixels 822 of the second test image 514' or a selected area 814 of the defect 516' (e.g., can also use X and Y coordinates in conjunction with these pixels 822) (block 428), which is demonstrated in FIG. 8. The second sensed image 514' can be superimposed over the first sensed image 514 (block 430) to provide a pictorial display or image 514" (block 432) to easily show the differences between the images, as shown in FIG. 9. The superimposed image can also be stored or saved as well to the storage device 623.

All embodiments of the present invention preferably include the step of contactingly transferring ultrasonic energy to the object 314 under test. To perform this step, for example, a piezo-electric material advantageously can be used for transferring the ultrasonic energy into the test object 314. A preferred preselected frequency to transfer the ultrasonic energy is about 20 kilohertz, for example. It will be understood by those skilled in the art, however, that other frequencies can be used as well to achieve selected results. The selection of the frequency depends on multiple parameters (like material, design, and structure of the test object) and can vary between about 1 kHz to 2000 kHz.

Several conditions can be varied in all embodiments of a method of enhancing the determination of the presence of a defect in an object 114, 114', 314 under test according to the present invention (see FIGS. 1–3). All embodiments of the method of enhancing the determination of the presence of a defect in an object under test preferably include directly applying a preselected contact force with an ultrasonic source 118, 118', 318' through which the ultrasonic energy is contactingly transferred to the object under test 114, 114', 314. An increase in the contact force increases the amount of ultrasonic energy that is transferred to the object under test 114, 114', 314. Once the contact force is increased to a certain level, the object under test 114, 114', 314 no longer vibrates due to the ultrasonic energy. During the transfer of the ultrasonic energy, the preselected direct contact force is preferably less than 80 pounds for many applications, e.g., combustion turbine blades. This preselected direct contact force of less than 80 pounds is believed to be an effective force that provides optimum energy to the object without halting the vibration of the object under test 114, 114', 314 due to contact pressure from the ultrasonic source 118, 118', 318'. In addition to varying the amount of force that is used for transferring the ultrasonic energy, the preselected time period that ultrasonic energy is transferred through the ultrasonic source can be varied depending on the application, for example. The preselected amplitude of the ultrasonic energy can also be altered. More than one of these conditions can be altered simultaneously.

FIGS. 3, 6A–6B, and 7 illustrate how a data comparator 624 of the computer 120, 120', 320 can organize the images that are captured, along with the settings for transferring the ultrasonic energy to the object 114, 114', 314' under test so that all of the data can be displayed simultaneously For example, the images in FIGS. 5A and 5B advantageously can be shown as selected images 712, 714, along with information about the amplitude at which the ultrasonic energy has been transferred as a first graph 716, the temperature of the determined defect as a second graph 718, and the power used to transfer the ultrasonic energy as a third graph 720. A control panel 722, e.g., as selectable icons, can also be displayed to assist a user in operating the system 100. The control panel 722 enables the user to perform such functions as varying the force in which the ultrasonic energy is applied to the object 114, 114', 314 under test or to save the images to a data storage device 623, such as the memory of the computer 120, 120', 320. As understood by those skilled in the art, the data appearing on the display 622 can be varied depending upon the user's preferences. The computer 320 preferably includes a processor 621 which can include therewith or as a separate device an image processor 323.

The present invention advantageously provides an alternate method of enhancing the determination of the presence of a defect in an object 114' under test, which is perhaps best shown in FIG. 2. The alternate method includes positioning an adhesive device 222 on at least portions of the object under test 114'. The adhesive device 222 advantageously defines a reference point, which is representative of a first defect in the object under test 114'. The method also includes transferring ultrasonic energy at a preselected frequency to the object under test 114'. The ultrasonic energy causes an increase in friction in portions of the object 114' adjacent a defect in the object, which increases the temperature of the portions adjacent the defect. A test image of the at least portions of an object 114' under test in an infrared spectrum is sensed. The test image preferably includes at least the reference point and a second defect. The second defect, for example, can be a naturally occurring defect, a manufacturing process defect, a defect due to damage to the object, or other occurring defects. The images advantageously can be compared by visibly identifying a plurality of different brightness levels between the portions of the object representative of the increased temperatures and surrounding regions thereof in the sensed test image. The increased temperature portions define a determined presence of the reference point and the second defect. The temperature gradient or difference in the area of the reference point advantageously can be compared to the second defect to the temperature gradient in the area where a defect is assumed.

The same data functions, shown in FIGS. 4A and 4B and described herein, can be used in this alternate method. This alternate method preferably includes receiving the sensed images of area of reference point and the tested area (block 412). The temperature gradient of the sensed reference point area and of the test area are determined by comparing the brightness levels with data from a temperature gradient or difference database and correlating a brightness level with a particular temperature (block 414). The temperature gradients of the reference point area and the tested area are displayed (block 416). A defect 516, 516' is identified or determined if the analysis of the temperature gradients show any significant difference to a defect free area or if temperature gradients in the tested area are comparable to those in the reference point area (block 418). The test image can be saved to a storage device (block 424) such as in a file format that will enable measuring the size of the second defect responsive to pixel count of the second defect (block 426), for example. It will also be understood by those skilled in the art, however, that other measuring techniques, such as scaled conversions of known object sizes and other techniques, can be used as well. The digital images of the reference point area and the defect area can also be superimposed (block 428) and displayed such as in a digital format (block 430) (see FIG. 9) or displayed in a side-by-side relationship, if desired (see FIG. 7). The superimposed digital images can also be analyzed (block 432).

The present invention also advantageously provides a system 100, 100' for detecting defects in an object under test 114, 114' as depicted in FIGS. 1–2. The object under test 114, 114' is intended to represent any structural component or material that may contain defects and can be particularly useful on metal components such as vanes or blades in the power generation industry. The object 114, 114', however, does not have to be metal, but can be other materials, such as ceramics or compositions, in other industries as well.

The system 100, 100' preferably includes a frame 116, 116' with an ultrasonic source 118, 118' mounted to the frame 116, 116'. The ultrasonic source 118, 118' can be any source suitable for the purposes described herein, such as an ultrasonic transducer or source by Branson Ultrasonics Corp. of Danbury, Conn. The ultrasonic source 118, 118' is preferably adapted to be positioned to abuttingly contact an object under test 114, 114' and to transmit ultrasonic energy to the object under test 114, 114' at a preselected frequency.

As shown in FIG. 6A, the system 100, 100' further preferably includes a computer 120, 120', 320 that contains a processor 621, a data storage device 623 in communication with the processor 621, a display 622 in communication with the processor 621, and a data comparator 624. The processor 621 is intended to include any type of processor that can carry out the functional requirements of the present invention. The data storage device 623 is intended to include any conventional random access memory device, read only memory device, or other memory the device as understood by those skilled in the art. The data comparator 624 is associated with the computer 322 and is adapted to compare sensed test images of the object 114, 114', 314 under test.

The system 100, 100' preferably includes a controller 124, 124', 324 in communication with the ultrasonic source 118, 118', 318 and the computer 120, 120', 320 to control the positioning and the pressure of the ultrasonic probe 118, 118', 318 responsive to the computer 120, 120', 320. The controller 124, 124', 324 preferably includes a motor 126, 126', a drive for the motor 128, 128', and an electronic interface 130, 130' in communication with the computer 120, 120', 320 to respond to preselected command signals from the computer 120, 120', 320 as also understood by those skilled in the art.

An infrared thermography camera 112, 112', 312 is another preferable component of the system 100, 100' of the present invention. The infrared thermography camera 112, 112' is positioned in communication with the computer 120, 120' and adapted to sense test images of the object under test 114, 114', 314 responsive to the computer 120, 120', 320. The infrared thermography camera 112, 112', 312 can be any camera suitable for the purposes described herein, such as those available from Indigo Systems Corp. of Santa Barbara, Calif., Raytheon Company of Lexington, Mass., or Honeywell International, Inc. of Morristown, N.J.

The system 100, 100' for detecting defects in an object under test 114, 114', 314 can also include a source mounting arm 132, 132'. The source mounting arm 132, 132' is preferably mounted to the frame 116, 116' and preferably is connected to the ultrasonic source 118, 118' to assist in positioning or moving the source 118, 118'. The source mounting arm 132, 132' is preferably in communication with the controller 124, 124' to position or move, e.g., raise, lower, extend, retract, or move laterally, the ultrasonic source 118, 118' responsive to the controller 124,124'.

In previous ultrasonic test methods, a coupler is sometimes required to protect the object 114, 114' under test from the vibration of the ultrasonic energy supplied to the object under test. There is no need for use of a coupler in the present invention since the pressure at which the ultrasonic energy is transferred to the object 114, 114' under test is controlled by the controller 124, 124' which has the ability to position and move the ultrasonic source 118, 118', thus increasing or decreasing the contact pressure, as needed. The maximum contact pressure/contact force can be limited to protect the object 114, 114' under test from damages.

As shown in FIG. 6B, the data comparator 624, for example, can include a first image determiner 626, a second image determiner 628, a temperature database 630, an image enhancer 632, a pixel counter 634, a defect size determiner 636, and an input/output device 638 as described above. The first image determiner 626 receives a first image from the infrared thermography camera 112, 112', 312 via the input/output device 638. The first image determiner 626 transfers the first image to the image enhancer 632. The second image determiner 628 receives a second image from the infrared thermography camera 112, 112', 312 via the input/output device 638. The second image determiner 628 transfers the first image to the image enhancer 632. The image enhancer 632 enhances images that the image enhancer 632 receives and sends the images to the input/output device 638. The pixel counter 634 measures the size of a predetermined defect based upon counting pixels with increased brightness levels and sends this measurement to the defect size determiner 636. The defect size determiner 636 correlates the pixel count to the size of the defect and sends this correlation to the input/output device 638. The temperature gradient database 630 determines a first temperature gradient of the first image and a second temperature gradient of the second image and sends the first and second temperature gradients to the input/output device 638. The input/output device 638 communicates with the display 622 by outputting data from the image enhancer 632 and the pixel counter 634 to the display 622.

The present invention also advantageously includes an additional component to the system 100' for detecting defects in an object under test, as shown in FIG. 2. The additional component is preferably an adhesive device 222. The adhesive device 222 is preferably adapted to be adhesively mounted to and abuttingly contact the object under test 114'. The adhesive device 222 defines a reference point representative of a defect in the object under test 114'. The adhesive device 222 of the alternate system 100' preferably includes a flexible substrate and an adhesive material positioned on the flexible substrate as understood by those skilled in the art. A preferred adhesive device 222 is tape, for example. Other adhesive devices known to those skilled in the art are to be considered within the scope of the present invention as well.

As an advantage of the present invention, inspection testing data can be obtained and evaluated in many different ways to determine if defects are present in material. The testing methods described herein are very accurate, less time consuming, and less expensive than traditional non-destructive testing methods. The new testing methods detect much smaller cracks than most non-destructive testing methods are capable of doing. Prior inspection testing methods can detect the presence of a defect, but often they do not allow for visually determining the size or extent of the defect and often require a coupler for use with many test devices.

Further advantages of the present invention include the data storage and trending that is available with this system 100, 100'. The data functions included in the present invention allow for greater analysis of the inspection testing data obtained from the images of the defects. The images can be viewed and stored electronically. The storage of the data allows inspection histories to be developed for objects to trend defects within an object. A permanent record of the inspection tests is obtained as a result of this system 100, 100'. The stored data can be used to monitor the defect to determine if it is getting worse and if it gets worse at what rate. Since many industries are required to maintain information of this type, it is advantageous that this system 100, 100' can be used to assist in compliance with these types of regulations.

Other advantages of the present invention include that the inspection process is fast and versatile. There are few material restrictions that the system 100, 100' can be used on, as compared to other previous systems. The modularity of the system 100, 100' allows multiple test configurations for a wide variety of test objects.

As a further advantage, the testing method and system 100, 100' are environmentally friendly. No chemicals are required as in some other non-destructive testing methods, such as dye penetrants. Real time images are available of the object under test.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed. For example, other industries, besides the power generation industry, can use this system for inspection purposes as well.

What is claimed is:

1. A method of enhancing the determination of the presence of a defect in an object under test, the method comprising the steps of:
    positioning an adhesive device on at least portions of the object under test, the adhesive device defining a reference point representative of a first defect in the object under test;
    transferring ultrasonic energy at a preselected frequency to the object under test so that the ultrasonic energy causes an increase in friction in portions of the object adjacent a defect in the object and thereby increases the temperature of the portions adjacent the defect;
    sensing a test image of the at least portions of an object under test in an infrared spectrum, the test image including at least the reference point and a second defect;
    identifying a plurality of different brightness levels between the portions of the object representative of the increased temperatures and surrounding regions thereof in the sensed test image so that the changed temperature gradients thereby define a determined presence of a defect; and
    comparing the reference point area to the temperature gradients of the tested area.

2. A method as defined in claim 1, further comprising measuring the temperature gradients of the sensed reference point area from the sensed test image, measuring the temperature gradients of the tested area, and comparing the temperature gradients of the reference point area with the temperature gradients of the tested area.

3. A method as defined in claim 2, further comprising storing the first test image in a storage device in a file format, and measuring the size of the identified defect responsive to pixel count of the sensed test image.

4. A method as defined in claim 1, wherein the step of transferring ultrasonic energy to the object under test includes utilizing a piezo-electric material for sourcing the ultrasonic energy at a preselected frequency.

5. A method as defined in claim 1, wherein the step of contactingly transferring ultrasonic energy to the object under test includes the following steps:
    directly applying a preselected contact force with an ultrasonic source through which the ultrasonic energy is contactingly transferred to the object under test during the transfer of the ultrasonic energy;
    transferring the ultrasonic energy for a preselected time period; and
    transferring the ultrasonic energy at a preselected frequency and amplitude.

6. A method as defined in claim 5, further comprising varying the amount of ultrasonic energy transferred to the object under test, the varying including at least one of the following: changing the amount of the preselected contact force applied to the object with the ultrasonic source, changing the preselected time period, and changing the preselected frequency and amplitude.

7. A system for enhanced determination of the presence of a defect in an object under test, the system comprising:
    an ultrasonic source adapted to be positioned to abuttingly contact an object under test and to transmit ultrasonic energy through the contact with the object under test at a preselected frequency;
    a computer comprising a processor, a data storage device in communication with the processor, and a monitor in communication with the processor;
    a controller in communication with the ultrasonic source and the computer to control the positioning of the ultrasonic source responsive to the computer;
    an infrared thermography camera positioned in communication with the computer and adapted to sense test images of the object under test responsive to the computer;
    an adhesive device adapted to be adhesively mounted to and abuttingly contact the object under test, the adhesive device defining a reference point representative of a defect in the object under test; and
    a data comparator adapted to compare test images of the object under test with the reference point.

8. A system as defined in claim 7, a telescopic arm connected to the ultrasonic source and in communication with the controller to extend or retract the ultrasonic source responsive to the controller.

9. A system as defined in claim 7, wherein the adhesive device includes a flexible substrate and an adhesive material positioned on the flexible substrate.

10. A system as defined in claim 7, wherein the data comparator comprises:

an image enhancer to enhance the first and second images of an object under test;

a first image determiner in communication with the image enhancer to receive the first enhanced image from the infrared thermography camera;

a second image determiner in communication with the image enhancer to receive the second enhanced image from the infrared thermography camera;

a temperature gradient database in communication with the first image determiner and the second image determiner to determine a first temperature gradient of the first image and a second temperature gradient of the second image;

a pixel counter to measure a size of a sensed defect to a pixel count; and a defect size determiner in communication with the pixel counter to correlate a pixel count with a size of the sensed defect.

* * * * *